United States Patent [19]

McAteer et al.

[11] Patent Number: 5,700,942
[45] Date of Patent: Dec. 23, 1997

[54] PROCESS FOR PREPARING QUINOLINE BASES

[75] Inventors: Colin H. McAteer, Indianapolis; Robert D. Davis, Sr., Greencastle; Joel R. Calvin, Westfield, all of Ind.

[73] Assignee: Reilly Industries, Inc., Indianapolis, Ind.

[21] Appl. No.: 678,155

[22] Filed: Jul. 11, 1996

[51] Int. Cl.$^6$ ................................ C07D 215/04
[52] U.S. Cl. ........................... 546/181; 546/152
[58] Field of Search ...................... 546/181, 152

[56] References Cited

U.S. PATENT DOCUMENTS

| | | | |
|---|---|---|---|
| 3,020,280 | 2/1962 | Cislak et al. | 260/283 |
| 3,020,281 | 2/1962 | Cislak et al. | 260/283 |
| 3,020,282 | 2/1962 | Cislak et al. | 260/283 |
| 4,439,607 | 3/1984 | Drabb | 546/89 |
| 4,617,395 | 10/1986 | Dockner et al. | 546/178 |
| 4,723,011 | 2/1988 | Doehner, Jr. | 546/250 |

*Primary Examiner*—Patricia L. Morris
*Assistant Examiner*—Charanjit S. Aulakh
*Attorney, Agent, or Firm*—Woodard, Emhardt, Naughton Moriarty & McNett

[57] ABSTRACT

There are provided processes for preparing quinolines by vapor phase reaction of a substituted or unsubstituted aniline base, formaldehyde and a $C_2$-$C_4$ aldehyde wherein the aldehydes:aniline base molar ratio is at least 2:1. More preferred processes of the invention achieve high selectivities and yields of 8-methylquinoline, and high conversions of the aniline base.

20 Claims, No Drawings

PROCESS FOR PREPARING QUINOLINE BASES

This application claims priority upon provisional U.S. patent application Ser. No. 60/001,049, filed Jul. 11, 1995, which is hereby incorporated by reference in its entirety.

BACKGROUND OF THE INVENTION

The present invention relates generally to quinoline bases, and in particular to vapor-phase reactions for preparing quinoline bases by reaction of aniline bases and aldehydes in the presence of solid acid catalysts.

As further background, quinoline bases such as 8-methylquinoline are known compounds which are useful as intermediates in the synthesis of agricultural and other chemicals. For example, it is known that 8-methylquinoline can be oxidized to form 2-acetylnicotinic acid (see C. O'Murchu, *Synthesis* 1989, pages 880–882), which itself serves as an intermediate to agricultural chemicals (see EP 646,315, Apr. 5, 1995).

The synthesis of 8-methylquinoline and other quinolines in good yield and selectivity so as to provide a commercial process has to date presented some difficulties. Quinolines are typically prepared by the "Skraup synthesis", a batch liquid-phase cyclo-condensation reaction of an arylamine, containing at least one unsubstituted ortho position to the amino group, with a glycerol in the presence of sulfuric acid, and an oxidizing agent. (See R. H. F. Manske and M. Kulka, and an oxidizing agent. (See R. H. F. Manske and M. Kulka, *Org. React.* 1953, p 59–98.) The Skraup synthesis is known to be an especially vigorous reaction and great care must be taken to moderate the reaction temperature by control of the glycerol and sulfuric acid addition rates. For this reason, the Skraup reaction is best carried out in batch on a small scale, or with apparatus designed to safeguard against uncontrolled addition of reagents and sudden reflux/vaporization of the reaction mixture, when preparing larger quantities of quinolines. When conditions are optimized, the Skraup synthesis can give good yields of quinolines, e.g. 90% yield of 8-methylquinoline (See, Synthesis 1989, 880–82). Even then, the Skraup synthesis has the major drawback of producing vast amounts of byproduct sodium sulfate upon work-up and neutralization of the reaction mixture. The weight of the sodium sulfate by-product typically exceeds the weight of the recovered quinoline compound by a factor of 3 to 6. The removal and safe disposal of contaminated sodium sulfate therefore becomes a significant concern should the quinoline compound be manufactured at the multi-ton scale.

Accordingly, there remains a need for convenient routes to quinolines characterized by high yields, selectivities and conversions, and preferably also by the production of this desired product in relatively high purity. Additionally, advantageous processes would produce organic by-products which can be incinerated as opposed to inorganic by-products which must be disposed to landfill or otherwise handled. The present invention addresses these needs.

SUMMARY OF THE INVENTION

It is an object of the present invention to provide processes for preparing quinolines by convenient, vapor phase reactions which result in high yields and conversions.

It is another object of the invention to provide a process for preparing quinolines which can be conveniently conducted using a broad range of available solid acid catalysts.

It is another object of the invention to provide processes for preparing quinolines which minimize the production of byproducts which may interfere with the recovery of the product or require costly disposal.

It is still another object of the invention to provide processes for preparing quinolines which are conveniently and effectively adapted to continuous operation in fixed or fluidized bed reaction systems.

These and other objects and advantages are provided by processes of the present invention, in which a quinoline base is prepared by passing a vapor stream containing aldehydes and an aniline base in a respective molar ratio of at least 2:1 over a solid acid catalyst bed at a temperature above about 350° C. so as to form the quinoline base, wherein the aldehydes include formaldehyde and a $C_2$–$C_4$ aldehyde. More preferred processes of the invention provide the preparation of alkyl-substituted quinoline bases, by reaction of an alkyl-substituted aniline with formaldehyde and a $C_2$–$C_4$ aldehyde. In a most preferred form the invention provides for the production of 8-methylquinoline, wherein 2-methylaniline (also known as ortho-toluidine), formaldehyde and acetaldehyde are reacted as above to form 8-methylquinoline. It has been discovered that such processes can be used to provide quinolines in surprisingly good yields while also achieving high conversions of the reactant materials. Moreover, it has been discovered that the utilization of excess aldehydes in the reactions increases the purity of the desired quinoline in the formed reacted mixture. For example, in the production of 8-methylquinoline, increasing the aldehydes:2-methylaniline molar ratio increases the amount of 8-methylquinoline formed relative to 2,8-dimethylquinoline—the latter being a compound which boils at a similar temperature to the desired product. Thus, the use of a substantial excess of the aldehydes leads to an improved workup procedure in which quinoline product can be recovered in good purity by distillation.

Another preferred embodiment of the invention provides a process for preparing 8-methylquinoline which includes passing formaldehyde, acetaldehyde and 2-methylaniline over a solid acid catalyst bed at a temperature of at least about 350° C. so as to form 8-methylquinoline. More preferred conditions for this process are similar to those discussed in connection with the above-mentioned embodiment of the invention.

These and still other objects, features and advantages of the invention will be apparent from the description which follows.

DESCRIPTION OF THE PREFERRED EMBODIMENT

For the purposes of promoting an understanding of the principles of the invention, reference will now be made to certain embodiments thereof and specific language will be used to describe the same. It will nevertheless be understood that no limitation of the scope of the invention is thereby intended, such alterations and further modifications of these embodiments, and such further applications of the principles of the invention as described herein being contemplated as would normally occur to one skilled in the art to which the invention relates.

As disclosed above, a preferred embodiment of the invention involves the reaction of one mole of an aniline base per two or more moles of aldehydes in the vapor phase in order to form a quinoline base. The applicant has discovered that this reaction achieves good conversions of the reactants while providing high yields and purities of and selectivities for the quinoline base product. In this regard, the starting materials for processes of the present invention are very readily available, and can be obtained from commercial sources or made by processes very well known to the art and literature. Thus, the term "aniline base" as used herein refers to substituted and unsubsituted aniline bases including aniline itself and substituted derivatives thereof which undergo the desired reaction to provide quinoline bases. Substituted anilines, when used, are preferably mono- or poly-alkyl-substituted wherein the alkyl group or groups contain from 1 to about 5 carbon atoms (i.e. $C_1$–$C_5$ alkyls), although those skilled in the pertinent field will recognize that other substituents which do not detrimentally interfere with the vapor phase reaction to form quinoline will be suitable. Most preferably, the aniline base is 2-methylaniline.

The aldehyde reactants will include formaldehyde and a $C_2$–$C_4$ aldehyde, e.g. acetaldehyde, propionaldehyde, or butyraldehyde, and these aldehydes, taken together, will be used in at least a 2:1 molar ratio with respect to the aniline base, and generally falling within the range of 2:1 to about 10:1. It has been discovered that the use of such high aldehyde:aniline base molar ratios not only provides excellent conversions of the aniline base, but also can be used to increase the selectivity of the process for the desired quinoline product.

In more preferred inventive processes, 2-methylaniline (ortho-toluidine), acetaldehyde and formaldehyde will be vaporized, either separately or together, and continuously passed over a catalyst bed to provide the desired 8-methylquinoline product. In one mode of carrying out the invention, the acetaldehyde and formaldehyde can be vaporized together and fed to the catalyst bed, and the 2-methylaniline can be vaporized and fed in a separate stream. This arrangement provides a convenient way to introduce the reactants to the catalyst bed, although many other suitable arrangements can be utilized as will be understood by and well within the purview of those practiced in the field.

In the production of 8-methylquinoline, as indicated above, the aldehydes (acetaldehyde and formaldehyde) will be provided to the reaction in at least a 2:1 molar ratio with respect to the 2-methylaniline. More preferred molar ratios of aldehydes to 2-methylaniline will be at least about 3:1. As indicated above and demonstrated in Table 2 below, such molar excesses of aldehyde lead to processes achieving high conversion of the aniline reactant, easily greater than 80% and even above 90% and approaching 100%. Moreover, increasing aldehyde:2-methylquinoline molar ratios leads to increasing 8-methylquinoline purity in the formed reaction mixture relative to the major by-product, 2,8-dimethylquinoline, with 8-methylquinoline:2,8-dimethylquinoline molar ratios above 10 easily being achieved in the formed reaction mixture. This of course improves workup of the reaction mixture, especially where distillation is involved.

The formaldehyde may originate from a feed material also containing methanol. In this regard, though, the applicant has discovered that increasing amounts of methanol fed to the reaction lead to decreasing productivities, selectivities, yields and purities for the desired 8-methylquinoline product, as demonstrated by the results shown in Table 3 below. It is therefore preferred from these standpoints that such feed contain a molar ratio of formaldehyde to methanol of at least about 1:1. Moreover, in preferred processes the molar ratio of the $C_1$ components (i.e. the moles of formaldehyde plus the moles of any methanol present) to acetaldehyde fed to the reaction will be at least about 1.

Water may also be included in one or more of the reactant feeds without substantially impacting the performance of the preferred inventive processes, as shown in Table 4 below in which a doubling of the water fed to the reaction led to no substantial change in the product yields. This will be advantageous in fluidized bed reactions in which steam is commonly employed to assist in maintaining the fluidization of the bed. In this regard, as indicated above, both these fluidized bed and fixed bed reaction systems are suitable for use in the present invention. The design and operation, and maintenance of both of these catalyst bed systems to achieve desirable production of quinolines will be well within the abilities of skilled artisans in the field. In the applicant's work thus far, fluidized bed reactions have provided preferred results.

The reactions of the invention will be conducted at temperatures sufficiently high to form the desired quinoline base product. Preferred temperatures will exceed about 350° C., for instance falling within the range of about 350° C. to about 550° C. More preferred temperatures for conducting the processes of the invention will be in the range of about 450° C. to about 500° C. Given the disclosures herein, the selection of optimal temperatures for a given reaction to achieve high 8-methylquinoline productivities while maximizing catalyst lifetime will be within the purview of the ordinarily skilled artisan.

Generally speaking, the catalyst used in the invention will be a solid catalyst which promotes the formation of the quinoline product in the reaction at hand. These catalysts will preferably be solid acid catalysts providing either Bronsted or Lewis acidity, with catalysts providing Bronsted acidity being preferred. More preferred catalysts will thus include amorphous silica-alumina catalysts as well as zeolite catalysts. In this regard, a broad variety of amorphous silica-alumina catalysts known and readily available from commercial sources. Similarly, various zeolite catalysts are also known and available, including for example medium-pore zeolites such as silicalite and ZSM-5 which have constraint indexes in the range of 1 to 12, as well as large pore zeolites such as zeolite-beta, zeolite-Y (including ultrastable-Y), and mordenite which have constraint indexes below 1. In accordance with the invention, zeolite or amorphous silica-alumina catalysts can be used in either their H-forms or can be modified with metals, for example zinc and tin, to modify their behavior in the reaction.

For use in the inventive processes, the solid acid catalysts are preferably formulated into a binder or matrix and then pelletized or extruded (with a fixed-bed catalyst) or ground or spray-dried (with a fluid-bed catalyst) to produce a form having commercial application. Such binders can be conventional and typically include, for example, naturally-occurring or synthetic materials such as clays (e.g. kaolin or montmorillonite), silica, alumina, silica-alumina, silica-magnesia, silica-zirconia, and ternary compositions such as silica-alumina-thoria, silica-alumina-zirconia, silica-alumina-magnesia, silica-magnesia-zirconia, and the like. As to amounts, the amount of binder (when used) in the formulated catalyst material will usually be up to about 80% w/w relative to a zeolite or amorphous silica-alumina catalyst. Especially for fluidized-bed operation, the resulting catalyst material will preferably have a particle size of about 5–500 µm, with an average particle size on the order of 60–100 µm being preferred.

The quinoline product can be recovered from the formed reaction mixtures and purified using conventional techniques such as distillation and the like. The product quinolines are suited for a broad variety of uses in the agricultural and other fields. For instance, 8-methylquinoline can be oxidized by ozone to form 2-acetylnicotinic acid. In such processes, the 8-methylquinoline is contacted with ozone followed by hydrogen peroxide under conditions effective to provide the 2-acetylnicotinic acid. Such processes are known, as is for example disclosed in *Synthesis* 1989, pages 880–882.

The following specific Examples are set forth to provide a greater understanding and appreciation of the present invention and its features and advantages. It will be understood that these Examples are illustrative and not limiting of the invention.

EXAMPLE 1

Catalyst Preparation

Most catalysts were provided in powder form and bound with 25–50% w/w of $SiO_2$ (Ludox AS-40, Du Pont Chemical). After drying and calcination (550° C. for 6 hours), the resulting cakes were crushed and sieved, and a 0.5 to 1.0 mm particle size material isolated and used. The binding treatment also converted zeolites in the ammonium form to the protonic or acidic form (H-form). $Al_2O_3$ (Alcoa H-151) and 4% w/w $Al_2O_3$:96% $SiO_2$ (Akzo) were provided in pellet form (about ¼ inch diameter) and were crushed and sieved to give a fraction with a 0.5 to 1.0 mm particle size range. An amorphous silica-alumina catalyst (13% w/w $Al_2O_3$:87% $SiO_2$, Grace) was modified with ZnO and $SnO_2$ using impregnation and precipitation methods. An aqueous zinc nitrate solution was added to this catalyst and after drying and calcination gave 8% w/w ZnO:12% $Al_2O_3$:80% $SiO_2$. A tin catalyst was prepared from tin(II) sulfate in the presence of aqueous ammonia and this silica-alumina catalyst. The slurry was recovered, dried and calcined to give 15% w/w $SnO_2$:11% $Al_2O_3$:74% $SiO_2$. The zinc- and tin-modified catalysts were bound with $SiO_2$ and an appropriately sized fraction prepared as described above. A listing of the catalysts used in these Examples is given in Table 1 below.

catalyst reuse) at 550° C. overnight. (18 hours) in flowing air. The temperature of the bed was then reduced to 470° C. The air flow was then replaced by nitrogen to purge the system for about 10 minutes, after which it was adjusted to achieve the selected contact time for the reaction.

The liquid feeds were provided via two separate syringe pumps. A first pump contained neat ortho-toluidine, while the second contained the formaldehyde:acetaldehyde solution. Formaldehyde solutions containing either 45% w/w formaldehyde:11% methanol:44% water or 52% w/w formaldehyde:2% methanol:46% water were used for the majority of the runs. Acetaldehyde (MeCHO), methanol and water were added to the formaldehyde solutions in order to obtain the desired feed compositions for the selected run.

The reactor effluent vapor was directed through a condenser and the recovered liquid was weighed at convenient times. Typically, the liquid obtained from the first 20 minutes of the run was discarded. Three one-hour test periods were then taken with the mid-point of each period representing 0.8, 1.8 and 2.8 hours-on-stream (HOS). The reaction crudes were homogenized with ethanol before adding 4-tert-butylpyridine as a standard. The samples were then analyzed by GC using standard techniques. The reported 8-methylquinoline selectivity and yield are based on the moles of ortho-toluidine. The purity of the 8-methylquinoline is based on the 8-methylquinoline/ 2,8-dimethylquinoline (2,8 -$Me_2Q$) weight ratio.

After completion of the run, the reactor unit was flushed with nitrogen. Zeolite catalysts were initially regenerated at 500° C. in 20% air/80% nitrogen gas for 30 minutes. The temperature was then increased to 550° C. and the proportion of air to nitrogen gas increased in stages until the catalyst was under a 100% atmosphere of air. The amorphous catalysts were taken through the same temperature program, but an atmosphere of 100% air was used throughout.

In a first set of Examples the molar ratio of aldehydes to ortho-toluidine (oTOL) was varied. For these Examples the

TABLE 1

| Catalyst Name | Source | Nominal Composition | % w/w $SiO_2$ Binder |
|---|---|---|---|
| LA | Grace low-alumina | 13% w/w $Al_2O_3$:87% $SiO_2$ | 20 |
| ZnO/LA | — | 8% w/w ZnO:12% $Al_2O_3$:80% $SiO_2$ | 20 |
| $SnO_2$/LA | — | 15% w/w $SnO_2$:11% $Al_2O_3$:74% $SiO_2$ | 20 |
| Alumina | Alcoa H-151 | $Al_2O_3$ | — |
| 4% $Al_2O_3$ | Akzo | 4% w/w $Al_2O_3$:96% $SiO_2$ | — |
| 3% $Al_2O_3$ | Engelhard B987-05 | 3% w/w $Al_2O_3$:97% $SiO_2$ | 20 |
| Silicalite | Union Carbide | $SiO_2/Al_2O_3 \geq 200$ | 20 |
| ZSM5 | PQ Corp CBV 3020 | $SiO_2/Al_2O_3 = 30$ | 20 |
| Zeolite-BETA | PQ Corp CP 811 BL-25 | $SiO_2/Al_2O_3 = 25$ | 20 |
| Mordenite (16) | Tosoh HSZ-630 HUA | $SiO_2/Al_2O_3 = 16$ | 20 |
| Zeolite-Y | PQ Corp CP 301-67 | $SiO_2/Al_2O_3 = 6$ | 20 |
| USY | Tosoh HSZ-390 HUA | $SiO_2/Al_2O_3 \geq 100$ | 20 |
| Mordenite (100) | Tosoh HSZ-690HOA | $SiO_2/Al_2O_3 = 100$ | 50 |
| Zeolite-L | PQ Corp. CP-L104 | $SiO_2/Al2O3 = 6$ | 20 |
| Ferrierite | PQ Corp. CP 904-20 | $SiO_2/Al_2O_3 = 15$ | 20 |

EXAMPLES 2–34

Fixed Bed Runs

A series of Examples were conducted to illustrate the production of 8-methylquinoline (8-MeQ) in accordance with the invention under varying conditions. Each Example used 8 mL of catalyst having a particle size range of 0.5–1.0 mm diameter. The catalyst bed was immobilized in a quartz tube held in place by two plugs of silica wool. Prior to the runs, the catalyst was activated (or regenerated in the case of LA catalyst was used at a bed temperature of 470° C. and a contact time of 3.1–3.6 seconds to produce 8-methylquinoline ($N_2$ carrier gas flow rate was adjusted to maintain contact time). A first liquid organic feed included 2-methylaniline (99.5% purity) provided at a flow rate of 1.0 mL/h. A second liquid feed included a $C_1$ component (formaldehyde:methanol in a 4.4:1 molar ratio) and acetaldehyde. The molar ratio of the $C_1$ component to acetaldehyde in this second feed was 1.1:1. The results are presented in Table 2 below.

TABLE 2

| Ex. | HOS | MeCHO/oTOL | % oTOL Conv | % Sel 8-MeQ | % Yield 8-MeQ | Productivity 8-MeQ g/g cat/h | 8-MeQ/2,8-Me$_2$Q |
|---|---|---|---|---|---|---|---|
| 2 | 0.8 | 0.5 | 53 | 28 | 15 | 0.06 | 5.5 |
|   | 1.8 |     | 43 | 33 | 14 | 0.06 | 5.1 |
|   | 2.8 |     | 48 | 29 | 14 | 0.06 | 4.8 |
| 3 | 0.8 | 0.6 | 54 | 24 | 13 | 0.05 | 6.4 |
|   | 1.8 |     | 50 | 28 | 14 | 0.06 | 7.0 |
|   | 2.8 |     | 53 | 26 | 14 | 0.06 | 7.0 |
| 4 | 0.8 | 0.8 | 57 | 35 | 20 | 0.08 | 7.1 |
|   | 1.8 |     | 53 | 36 | 19 | 0.08 | 7.4 |
|   | 2.8 |     | 55 | 44 | 24 | 0.10 | 7.8 |
| 5 | 0.8 | 1.0 | 49 | 51 | 25 | 0.11 | 8.2 |
|   | 1.8 |     | 65 | 28 | 18 | 0.08 | 9.2 |
|   | 2.8 |     | 69 | 29 | 20 | 0.08 | 11 |
| 6 | 0.8 | 2.0 | 85 | 44 | 37 | 0.16 | 12 |
|   | 1.8 |     | 90 | 47 | 42 | 0.17 | 15 |
|   | 2.8 |     | 92 | 48 | 44 | 0.19 | 18 |
| 7 | 0.8 | 3.0 | 94 | 47 | 44 | 0.19 | 15 |
|   | 1.8 |     | 97 | 48 | 47 | 0.20 | 25 |
|   | 2.8 |     | 98 | 51 | 50 | 0.21 | 35 |
| 8 | 0.8 | 4.0 | 98 | 43 | 42 | 0.17 | 23 |
|   | 1.8 |     | 99 | 54 | 53 | 0.22 | 44 |
|   | 2.8 |     | 99 | 55 | 54 | 0.23 | 61 |

The data in Table 2 demonstrate that increasing acetaldehyde/ortho-toluidine molar ratios benefit the 8-methylquinoline selectivity, yield and productivity. In addition, acetaldehyde/ortho-toluidine molar ratios of $\geq 2$ gave very high conversion of ortho-toluidine and improved 8-methylquinoline product purity as shown by the 8-methylquinoline/2,8-Me$_2$Q weight ratio. The 2,8-Me$_2$Q (b.pt.=255° C.) is the primary impurity which needs to be minimized upon distillation of the 8-methylquinoline (b.pt= 248° C.).

In another set of runs the LA catalyst was used under similar conditions, except that the contact time was 3.6–4.2 seconds, the acetaldehyde to ortho-toluidine molar ratio was held at about 3:1, and the formaldehyde to methanol molar ratio was varied. The result are presented in Table 3 below.

Table 3 demonstrates that a 52% CH$_2$O/2% CH$_3$OH/46% H$_2$O mixture gave the best results for ortho-toluidine conversion, 8-methylquinoline yield and purity. Partial replacement of the formaldehyde by methanol (CH$_2$O/CH$_3$OH=1.0–4.4) gives intermediate 8-methylquinoline selectivities, yields, productivities and purities. Complete replacement of the formaldehyde by methanol (CH$_2$O/CH$_3$OH=0.0) gives product, but with a relatively poorer yield and purity.

Another set of runs was conducted to demonstrate the effect of added water on the reaction. The conditions were similar to those for Example 7 described above (MeCHO/oTOL=3.0) except water was fed in the amounts shown in Table 4.

TABLE 3

| Ex. | HOS | CH$_2$O/CH$_3$OH | % oTOL Conv | % Sel 8-MeQ | % Yield 8-MeQ | Productivity 8-MeQ g/g cat/h | 8-MeQ/2,8-Me$_2$Q |
|---|---|---|---|---|---|---|---|
| 9 | 0.8 | 27.7 | 100 | 62 | 62 | 0.23 | 45 |
|   | 1.8 |      | 100 | 63 | 63 | 0.23 | 84 |
|   | 2.8 |      | 100 | 66 | 66 | 0.24 | 101 |
| 10 | 0.8 | 4.4 | 94 | 47 | 44 | 0.19 | 15 |
|    | 1.8 |     | 97 | 48 | 47 | 0.20 | 25 |
|    | 2.8 |     | 98 | 51 | 50 | 0.21 | 35 |
| 11 | 0.8 | 1.0 | 95 | 48 | 46 | 0.18 | 9.5 |
|    | 1.8 |     | 99 | 53 | 52 | 0.20 | 13 |
|    | 2.8 |     | 99 | 55 | 54 | 0.21 | 16 |
| 12 | 0.8 | 0.0 | 87 | 36 | 31 | 0.12 | 8.2 |
|    | 1.8 |     | 91 | 39 | 34 | 0.13 | 9.1 |
|    | 2.8 |     | 94 | 35 | 33 | 0.13 | 9.8 |

TABLE 4

| Ex. | HOS | H₂O/ oTOL | % oTOL Conv | % Sel 8-MeQ | % Yield 8-MeQ | Productivity 8-MeQ g/g cat/h | 8-MeQ/2,8-Me₂Q |
|---|---|---|---|---|---|---|---|
| 13 | 0.8 | 4.3 | 94 | 47 | 44 | 0.19 | 15 |
|  | 1.8 |  | 97 | 48 | 47 | 0.20 | 25 |
|  | 2.8 |  | 98 | 51 | 50 | 0.21 | 35 |
| 14 | 0.8 | 8.6 | 98 | 51 | 50 | 0.21 | 24 |
|  | 1.8 |  | 98 | 51 | 50 | 0.21 | 37 |
|  | 2.8 |  | 98 | 51 | 50 | 0.21 | 46 |

As can be seen, doubling the H₂O/ortho-toluidine ratio is possible without impacting the yield and moreover it appears to improve the purity to some extent.

In another set of experiments various C₃ feed components were investigated in place of the formaldehyde:acetaldehyde feed (C₃/oTOL molar ratio=1). The conditions were the same as those for the first set of runs above (Examples 2–8) except where otherwise indicated. The results are shown in Table 5.

TABLE 5

| Ex. | HOS | Feed | H₂O/C₃ | CT sec | % oTOL Conv | % Sel 8-MeQ | % Yield 8-MeQ | Productivity 8-MeQ g/g cat/h | 8-MeQ/ 2,8-Me₂Q |
|---|---|---|---|---|---|---|---|---|---|
| 15 | 0.0 | CH₂O/MeCHO* | N/A | 3.5 | 49 | 51 | 25 | 0.11 | 8.2 |
|  | 1.8 |  |  | 3.5 | 65 | 28 | 15 | 0.08 | 9.2 |
|  | 2.8 |  |  | 3.5 | 69 | 29 | 20 | 0.08 | 11 |
| 16 | 0.8 | Acrolein | 0.0 | 2.3 | 87 | 5 | 4 | 0.01 | 26 |
|  | 1.8 |  |  | 1.9 | 65 | 15 | 12 | 0.04 | 15 |
|  | 2.8 |  |  | 3.8 | 79 | 8 | 6 | 0.02 | 42 |
| 17 | 0.8 | Acrolein | 14.2 | 2.0 | 49 | 22 | 11 | 0.05 | 9.1 |
|  | 1.8 |  |  | 1.9 | 49 | 31 | 15 | 0.08 | 26 |
| 18 | 0.8 | Allyl alcohol | 0.4 | 6.9 | 57 | 2 | 1 | 0.01 | 5.3 |
|  | 1.0 |  |  | 6.9 | 64 | 2 | 1 | 0.01 | 1.1 |
| 19 | 2.8 | Glycerol | 0.0 | 2.9 | 70 | 11 | 8 | 0.04 | 9.6 |
|  | 3.8 |  |  | 2.3 | 87 | 10 | 9 | 0.04 | 18 |

*MeCHO/oTOL = 1.0

As can be seen, the C₃ compounds did provide amounts of the 8-methylquinoline product, but the overall processes were relatively inferior when compared to the reactions employing the formaldehyde/acetaldehyde feed.

In still further runs conducted generally as described above, various catalysts were employed instead of the LA catalyst, with MeCHO/oTOL and C₁/MeCHO mole ratios of 3.0 and 1.1, respectively, and a contact time of 3.6 seconds. The results are set forth in Table 6 below and demonstrate the efficacy of a broad range of solid acid catalysts for preparing the quinoline product.

TABLE 6

| Ex. | Catalyst | HOS | % oTOL Conv | % Sel 8-MeQ | % Yield 8-MeQ | Prod 8-MeQ g/g cat/h | 8-MeQ/2,8-Me₂Q |
|---|---|---|---|---|---|---|---|
| 20 | 13% Al₂O₃/87% SiO₂ (Grace) | 0.8 | 94 | 47 | 44 | 0.19 | 15 |
|  |  | 1.8 | 97 | 48 | 47 | 0.20 | 25 |
|  |  | 2.8 | 98 | 51 | 50 | 0.21 | 35 |
| 21 | 8% ZnO/12% Al₂O₃/80% SiO₂ | 0.8 | 97 | 48 | 47 | 0.15 | 16 |
|  |  | 1.8 | 97 | 52 | 50 | 0.16 | 27 |
|  |  | 2.8 | 96 | 51 | 49 | 0.15 | 38 |
| 22 | 15% SnO₂/11% Al₂O₃/74% SiO₂ | 0.8 | 97 | 46 | 45 | 0.16 | 12 |
|  |  | 1.8 | 98 | 49 | 48 | 0.17 | 16 |
|  |  | 2.8 | 98 | 47 | 46 | 0.16 | 21 |
| 23 | Alumina (Alcoa) | 0.8 | 39 | 15 | 6 | 0.01 | 3.8 |
|  |  | 1.8 | 36 | 11 | 4 | 0.01 | 4.4 |
|  |  | 2.8 | 38 | 13 | 5 | 0.01 | 5.5 |
| 24 | 4% Al₂O₃/96% SiO₂ (Akzo) | 0.8 | 96 | 70 | 67 | 0.36 | 21 |
|  |  | 1.8 | 98 | 60 | 59 | 0.31 | 34 |

TABLE 6-continued

| Ex. | Catalyst | HOS | % oTOL Conv | % Sel 8-MeQ | % Yield 8-MeQ | Prod 8-MeQ g/g cat/h | 8-MeQ/2,8-Me$_2$Q |
|---|---|---|---|---|---|---|---|
| | | 2.8 | 98 | 61 | 60 | 0.32 | 46 |
| 25 | 3% Al$_2$O$_3$/97% SiO$_2$ | 0.8 | 96 | 56 | 54 | 0.15 | 18 |
| | (Engelhard) | 1.8 | 96 | 58 | 56 | 0.16 | 29 |
| | | 2.8 | 97 | 61 | 59 | 0.17 | 37 |
| 26 | Silicalite | 0.8 | 92 | 21 | 19 | 0.05 | 48 |
| | (Union Carbide) | 1.8 | 94 | 22 | 21 | 0.05 | 42 |
| | | 2.8 | 93 | 25 | 23 | 0.06 | 47 |
| 27 | Zeolite-Beta (SiO$_2$/Al$_2$O$_3$ | 0.8 | 96 | 55 | 53 | 0.25 | 18 |
| | = 25) | 1.8 | 97 | 57 | 55 | 0.24 | 33 |
| | (PQ Corp.) | 2.8 | 97 | 54 | 53 | 0.25 | 39 |
| 28 | H-ZSM5 (SiO$_2$/Al$_2$O$_3$ = 30) | 0.8 | 91 | 47 | 42 | 0.14 | 9 |
| | (PQ Corp.) | 1.8 | 96 | 52 | 50 | 0.16 | 47 |
| | | 2.8 | 98 | 52 | 51 | 0.17 | 54 |
| 29 | H-Mordenite (SiO2/Al2O3 | 0.8 | 98 | 17 | 17 | 0.05 | 51 |
| | – 16) | 1.8 | 96 | 31 | 30 | 0.09 | 38 |
| | (Tosoh Corp.) | 2.8 | 96 | 30 | 20 | 0.09 | 55 |
| 30 | H-Y | 0.8 | 97 | 30 | 29 | 0.11 | 12 |
| | (PQ Corp.) | 1.8 | 98 | 54 | 53 | 0.20 | 52 |
| | | 2.8 | 98 | 51 | 50 | 0.19 | 58 |
| 31 | USY | 0.8 | 98 | 43 | 42 | 0.18 | 35 |
| | (Tosoh Corp.) | 1.8 | 98 | 42 | 41 | 0.17 | 45 |
| | | 2.8 | 96 | 47 | 45 | 0.19 | 45 |
| 32 | H-Mordenite (SiO$_2$/Al$_2$O$_3$ = 100) | 0.8 | 98 | 33 | 32 | 0.11 | 39 |
| | (Tosoh Corp.) | 1.8 | 96 | 42 | 40 | 0.14 | 42 |
| | | 2.8 | 96 | 41 | 39 | 0.14 | 38 |
| 33 | H-Ferrierite (SiO2/Al2O3 = 15) | 0.8 | 98 | 33 | 32 | 0.11 | 33 |
| | (PQ Corp.) | 1.8 | 96 | 42 | 40 | 0.14 | 43 |
| | | 2.8 | 96 | 41 | 39 | 0.14 | 89 |
| 34 | Zeolite-L | 0.8 | 84 | 2 | 2 | 0 | 1 |
| | (PQ Corp.) | 1.8 | 86 | 2 | 2 | 0 | 1 |
| | | 2.8 | 88 | 1 | 1 | 0 | 1 |

EXAMPLE 35

Fluid-Bed Reaction

The as-received powder form of the LA catalyst (440 gm) was loaded into a 1.6" internal diameter fluid-bed reactor. Fluidization of the catalyst bed was initiated by passing nitrogen gas through a distributor plate at the base of the reactor. The reactor was then brought up to 470° C. The formaldehyde/acetaldehyde ($C_1/C_2$=1.1 molar) solution and ortho-toluidine were pumped separately into the reactor. The formaldehyde/acetaldehyde solution was passed through a vaporizer before entering the reactor via a sparger line. The ortho-toluidine was also vaporized and fed together with the nitrogen through the distributor plate. The superficial velocity through the reactor was 1 ft/second with acetaldehyde/ortho-toluidine and $N_2$/(oTOL+MeCHO+CH$_2$O+MeOH) molar ratios of 3.65 and 1.0, respectively.

The reactor effluent was passed through a filter head before being condensed and collected in the receiver. The liquid recovered from the first 15 minutes of operation was discarded. The liquid reaction crude was then collected for 105 minutes. At the end of the run, the reactor was purged with nitrogen before regenerating the catalyst with air at 550° C. The recovered liquid reaction crude was analyzed in the same fashion as that described for the fixed-bed catalyst testing. It showed that the ortho-toluidine conversion was 99.7% with an 8-methylquinoline yield of 67.8%.

The 8-methylquinoline, along with other quinoline bases, was recovered from the wet reaction crude by toluene extraction. The toluene was distilled from the extract to give a dried crude which was distilled at reduced pressure. An 8-methylquinoline fraction was collected at 143° C. and 34 mm Hg pressure. Analysis of collected 8-methylquinoline fractions showed that over 85% recovery was obtained. The assay of the mid-fraction of the 8-methylquinoline had an assay of 96%.

EXAMPLES 36–56

Synthesis of Additional Quinolines

These runs set forth results of fixed-bed microreactor reactions for the synthesis of 3-methylquinoline (3-MeQ), 3-ethylquinoline (3-EtQ), 3,8-dimethylquinoline (3,8-Me$_2$Q), mixtures containing 3,7-dimethylquinoline (3,7-Me$_2$Q) and 3,5-dimethylquinoline (3,5-Me$_2$Q), mixtures containing 7-methylquinoline and 5-methylquinoline, 6,8-dimethylquinoline, and 8-isopropylquinoline (8-IPQ). These products were formed by the reaction of a mixed C$_1$/RCH$_2$CHO feed (R=Me, Et) with an arylamine feed (arylamine fed at 1.0 mL/hr), as indicated in the Tables below. The arylamines used included: aniline (PhNH$_2$), ortho-toluidine (oTOL), meta-toluidine (mTOL), 2,4-dimethylaniline (2,4-Me$_2$A), and 2-isopropylaniline (2-IPA). All of the run data were obtained with a bed volume of 8 mL, a particle size range of 0.5–1.0 mm and a bed temperature of 470° C. The RCH$_2$CHO/arylamine and C$_1$/RC$_2$CHO mole ratios were 3.0 and 1.1, respectively, and the C$_1$ feeds used had a CH$_2$O/CH$_3$OH mole ratio of 4.4. A nitrogen carrier gas was used to maintain a contact time between 3.0 and 4.0 seconds.

The catalysts used in these runs were essentially the same as those reported in the examples above, and are listed in Table, 7 below. Different $SiO_2/Al_2O_3$ ratios were used for the ZSM5 (MFI) and zeolite-BETA (BEA) catalysts. The silica binding, drying, calcination and sieving steps are identical to those reported in the Examples above.

TABLE 7

| Catalyst name | Abbrev. | Supplier/ Code | Nominal Composition | % wt $SiO_2$ Binder |
|---|---|---|---|---|
| Grace-LA | LA | Grace low-alumina | 13% w/w $Al_2O_3$: 87% $SiO_2$ | 20 |
| ZSM5 | MFI(80) | PQ Corp. CBV 8020 | $SiO_2/Al_2O_3 = 80$ | 20 |
| Zeolite-BETA | BEA(75) | PQ Corp. CP 811BL-75 | $SiO_2/Al_2O_3 = 75$ | 20 |
| Zeolite-Y | H-Y | PQ Corp. CP 301-67 | $SiO_2/Al_2O_3 = 6$ | 20 |
| Mordenite | MOR(100) | Tosoh HSZ-690HOA | $SiO_2/Al_2O_3 = 100$ | 50 |

TABLE 8

3-Methylquinoline Production
Contact time = 3.4–3.7 seconds
Liquid Feed 1: $PhNH_2$
Liquid Feed 2: $C_1/EtCHO$

| Ex. | Catalyst | HOS | % $PhNH_2$ Conv | % Sel 3-MeQ | % Yield 3-MeQ | Prod 3-MeQ g/g cat/h |
|---|---|---|---|---|---|---|
| 36 | LA | 0.8 | 99 | 60.5 | 59.8 | 0.29 |
|  |  | 1.8 | 99 | 73.3 | 72.3 | 0.35 |
|  |  | 2.8 | 98 | 77.0 | 75.5 | 0.36 |
| 37 | MOR(100) | 0.8 | 98 | 61.1 | 59.7 | 0.26 |
|  |  | 1.8 | 99 | 64.4 | 63.5 | 0.28 |
|  |  | 2.8 | 99 | 60.9 | 60.5 | 0.27 |
| 38 | BEA(75) | 0.8 | 99 | 68.2 | 67.7 | 0.38 |
|  |  | 1.8 | 99 | 71.8 | 70.9 | 0.40 |
|  |  | 2.8 | 99 | 73.6 | 72.6 | 0.41 |
| 39 | H-Y | 0.8 | 98 | 51.5 | 50.6 | 0.24 |
|  |  | 1.8 | 98 | 55.9 | 54.8 | 0.26 |
|  |  | 2.8 | 98 | 58.0 | 57.1 | 0.27 |
| 40 | MFI(80) | 0.8 | 99 | 52.0 | 51.8 | 0.15 |
|  |  | 1.8 | 99 | 57.0 | 56.7 | 0.17 |
|  |  | 2.8 | 99 | 51.7 | 51.5 | 0.15 |

TABLE 9

3-Ethylquinoline Production
Contact time = 3.4–3.6 seconds
Liquid Feed 1: $PhNH_2$
Liquid Feed 2: $C_1/PrCHO$

| Ex. | Catalyst | HOS | % $PhNH_2$ Conv | % Sel 3-EtQ | % Yield 3-EtQ | Prod 3-EtQ g/g cat/h |
|---|---|---|---|---|---|---|
| 41 | LA | 0.8 | 98 | 49.3 | 48.6 | 0.26 |
|  |  | 1.8 | 99 | 57.3 | 56.8 | 0.30 |
|  |  | 2.8 | 99 | 59.1 | 58.8 | 0.31 |
| 42 | MOR(100) | 0.8 | 98 | 57.1 | 56.2 | 0.27 |
|  |  | 1.8 | 98 | 53.9 | 52.8 | 0.26 |
|  |  | 2.8 | 97 | 55.7 | 54.0 | 0.26 |
| 43 | BEA(75) | 0.8 | 99 | 37.3 | 37.0 | 0.23 |
|  |  | 1.8 | 99 | 38.6 | 38.1 | 0.24 |
|  |  | 2.8 | 98 | 30.6 | 30.1 | 0.19 |
| 44 | H-Y | 0.8 | 99 | 72.3 | 72.0 | 0.38 |
|  |  | 1.8 | 99 | 71.5 | 71.0 | 0.37 |
|  |  | 2.8 | 99 | 64.9 | 64.6 | 0.34 |
| 45 | MFI(80) | 0.8 | 99 | 33.8 | 33.6 | 0.11 |
|  |  | 1.8 | 99 | 53.5 | 53.3 | 0.17 |
|  |  | 2.8 | 99 | 54.4 | 54.0 | 0.18 |

TABLE 10

3,7- and 3,5-Dimethylquinoline Production.
Contact time = 3.8–3.9 seconds
Liquid Feed 1: mTOL
Liquid Feed 2: $C_1/EtCHO$

| Ex. | Catalyst | HOS | % mTOL Conv | % Sel (3,7-$Me_2Q$ + 3,5-$Me_2Q$) | % Yield (3,7-$Me_2Q$ + 3,5-$Me_2Q$) | Ratio (3,7-$Me_2Q$/ 3,5-$Me_2Q$) | Prod 3,7- + 3,5- $Me_2Q$ g/g cat/h |
|---|---|---|---|---|---|---|---|
| 46 | MOR(100) | 0.8 | 96 | 48.7 | 46.9 | 2.2 | 0.18 |
|  |  | 1.8 | 96 | 40.6 | 39.1 | 2.1 | 0.18 |
|  |  | 2.8 | 96 | 39.2 | 37.7 | 2.1 | 0.19 |
| 47 | BEA(75) | 0.8 | 99 | 47.9 | 47.6 | 2.2 | 0.34 |
|  |  | 1.8 | 99 | 58.3 | 58.0 | 2.1 | 0.34 |
|  |  | 2.8 | 99 | 58.9 | 58.5 | 2.1 | 0.34 |
| 48 | HY | 0.8 | 99 | 46.2 | 45.8 | 1.9 | 0.19 |
|  |  | 1.8 | 99 | 34.5 | 34.3 | 1.9 | 0.15 |
|  |  | 2.8 | 99 | 31.9 | 31.7 | 1.8 | 0.14 |
| 49 | MFI(80) | 0.8 | 99 | 54.5 | 53.9 | 1.9 | 0.15 |
|  |  | 1.8 | 99 | 56.3 | 55.9 | 2.0 | 0.20 |

TABLE 11

Production of Various Quinolines Over LA
Contact time = 3.2–4.0 sec
Liquid Feed 1: ArNH$_2$
Liquid Feed 2: C$_1$/RCH$_2$CHO

| Ex | ArNH$_2$ | RCHO | HOS | RCHO ArNH$_2$ (molar) | Desired Compound | % Conv ArNH$_2$ | % Yield | Ratio |
|---|---|---|---|---|---|---|---|---|
| 50 | PhNH$_2$ | CH$_2$O— | 0.8 | 1.1 | Quinoline | 64 | 23 | — |
|    |          | MeCHO   | 1.8 | 3.3 |           | 99 | 51 | — |
| 51 | OTOL     | CH$_2$O— | 3.8 | 1.0 | 3,8-Me$_2$Q | 67 | 58 | — |
|    |          | EtCHO   |     |     |           |    |    |    |
| 52 | mTOL     | CH$_2$O— | 0.8 | 3.0 | 7-MeQ- | 93 | 29 | ≈2 |
|    |          | MeCHO   | 1.8 | 3.0 | major  | 99 | 26 | ≈2 |
|    |          |         | 2.8 | 3.0 | 5-MeQ- minor | 99 | 26 | ≈2 |
| 53 | 2,4-     | CH$_2$O— | 0.8 | 3.3 | 6,8-Me$_2$O | 98 | 25 | — |
|    | Me$_2$A  | MeCHO   | 1.8 | 3.3 |           | 96 | 28 | — |
| 54 | 2-       | CH$_2$O— | 0.9 | 3.1 | 8-IPQ | 98 | 28 | — |
|    | IPAN     | MeCHO   | 1.9 | 3.1 |       | 97 | 32 | — |
|    |          |         | 2.8 | 3.1 |       | 96 | 32 | — |

The above data demonstrate that good yields and selectivities of 3-alkylquinolines are obtained in accordance with the invention with a range of solid acid catalysts. In addition, in two further runs, inventive processes were used to prepare 3,8-dimethylquinoline over the MOR(100) (Example 55) and H-Y (Example 56) catalysts, respectively. In particular, under the conditions specified for Table 10, except substituting ortho-toluidine for meta-toluidine, 3,8-dimethylquinoline was produced with resultant good conversions, selectivities, yields and productivities over these two catalysts.

What is claimed is:

1. A process for preparing quinoline bases which comprises passing a vapor stream containing aldehydes and an aniline base in a respective molar ratio of at least 2:1 over a solid acid catalyst bed at a temperature above about 350° C. so as to form a quinoline base, said aldehydes including formaldehyde and a C$_2$–C$_4$ aldehyde.

2. The process of claim 1 wherein the vapor stream also includes methanol and wherein the molar ratio of formaldehyde plus methanol to the C$_2$–C$_4$ aldehyde is at least about 1.

3. The process of claim 2 wherein the vapor stream comprises an alkyl-substituted aniline, and also comprising the step of recovering an alkyl-substituted quinoline as a product of said reacting.

4. The process of claim 3 wherein the alkyl-substituted aniline is a 2-alkylaniline.

5. The process of claim 3 wherein the alkyl-substituted aniline is a methylaniline.

6. The process of claim 5 wherein the methylaniline is 2-methylaniline.

7. A process for preparing 8-methylquinoline, comprising passing a vapor stream containing 2-methylaniline, formaldehyde and acetaldehyde over a solid acid catalyst bed at a temperature above about 350° C. so as to form 8-methylquinoline, wherein the molar ratio of formaldehyde and acetaldehyde taken together to 2-methylaniline is at least 2:1.

8. The process of claim 7 wherein said temperature is in the range of about 400° C. to about 550° C.

9. The process of claim 8 wherein said vapor stream also contains water.

10. The process of claim 9 wherein said vapor stream also contains methanol, and wherein the molar ratio of formaldehyde and methanol taken together to acetaldehyde is at least about 1.

11. The process of claim 10 wherein said solid acid catalyst bed contains an amorphous silica-alumina catalyst or zeolite catalyst.

12. The process of claim 11 wherein said catalyst bed is a fixed bed.

13. The process of claim 11 wherein said catalyst bed is a fluidized bed.

14. The process of claim 11 wherein the 8-methylquinoline is formed in a yield of at least about 50%.

15. The process of claim 14 wherein said 8-methylquinoline is formed in a molar ratio of at least 10:1 relative to 2,8-dimethylquinoline.

16. The process of claim 15 wherein said molar ratio of formaldehyde and acetaldehyde taken together to 2-methylaniline is at least about 3:1.

17. The process of claim 12 wherein said vapor stream contains acetaldehyde and 2-methylaniline in a molar ratio of at least about 2:1.

18. A process for preparing 8-methylquinoline, comprising the steps of:

passing a vapor stream containing 2-methylaniline, formaldehyde and acetaldehyde over a solid acid catalyst bed at a temperature above about 350° C. so as to form a reacted mixture containing 8-methylquinoline, wherein the molar ratio of formaldehyde and acetaldehyde taken together to 2-methylaniline is at least 2:1; and purifying the 8-methylquinoline by distillation.

19. The process of claim 18 wherein said temperature is in the range of about 400° C. to about 500° C., and wherein said vapor stream also contains water.

20. The process of claim 19 wherein:

said solid acid catalyst bed is a fluidized bed containing an amorphous silica-alumina catalyst or a zeolite catalyst, wherein said molar ratio of formaldehyde and acetaldehyde taken together to 2-methylaniline is at least about 3:1, and wherein 8-methylquinoline and 2,8-dimethylquinoline are formed in said reacted mixture in a molar ratio of at least about 10:1, respectively.

* * * * *

UNITED STATES PATENT AND TRADEMARK OFFICE
CERTIFICATE OF CORRECTION

PATENT NO : 5,700,942

DATED : December 23, 1997

INVENTOR(S) : Colin H. McAteer et al.

It is certified that error appears in the above-identified patent and that said Letters Patent is hereby corrected as shown below:

In Table 1, in the column entitled "Catalyst Name", row 8, please delete "ZSMS" and insert in lieu thereof —ZSM5—.

In Table 5, under the column entitled "HOS", row 1, please delete "0.0" and insert in lieu thereof —0.8—.

In Table 5, under the column entitled "% Sel 8-MeQ", row 5, please delete "15" and insert in lieu thereof —18—.

In Table 5, under the column entitled "% Yield 8-MeQ", row, 2, please delete "15" and insert in lieu thereof —18—

In col. 12, line 61, please delete "$C_1/RC_2$" and insert in lieu thereof —$C_1/RCH_2$—.

In Table 10, under the column entitled "Catalyst", row 3, please delete "HY" and insert in lieu thereof —H-Y—.

In Table 11, under the column entitled "$ArNH_2$", please delete "OTOL" and insert in lieu thereof —oTOL—.

UNITED STATES PATENT AND TRADEMARK OFFICE
CERTIFICATE OF CORRECTION

PATENT NO. : 5,700,942
DATED : December 23, 1997
INVENTOR(S) : Colin H. McAteer et al.

It is certified that error appears in the above-indentified patent and that said Letters Patent is hereby corrected as shown below:

In Table 11, under the column entitled "Desired Compound", please delete "6,8-Me$_2$O" and insert in lieu thereof —6,8-Me2Q—.

In Table 11, under the column entitled "% Conv ArNH$_2$", row 4, please delete "93" and insert in lieu thereof —99—.

Signed and Sealed this

Sixteenth Day of November, 1999

Attest:

Q. TODD DICKINSON

Attesting Officer

Acting Commissioner of Patents and Trademarks